(12) United States Patent
Toth et al.

(10) Patent No.: US 6,307,918 B1
(45) Date of Patent: Oct. 23, 2001

(54) POSITION DEPENDENT BEAM QUALITY X-RAY FILTRATION

(75) Inventors: Thomas L. Toth, Brookfield; Carmine F. Vara, New Berlin; Willi W. Hampel, St. Francis, all of WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/140,112

(22) Filed: Aug. 25, 1998

(51) Int. Cl.7 ....................................................... G21K 3/00
(52) U.S. Cl. ........................... 378/158; 378/156; 378/159
(58) Field of Search .................................... 378/156, 158, 378/159

(56) References Cited

U.S. PATENT DOCUMENTS

| | | | |
|---|---|---|---|
| 3,860,817 | * 1/1975 | Carmean | 250/320 |
| 4,868,843 | * 9/1989 | Nunan | 378/152 |
| 4,975,933 | * 12/1990 | Hampel | 378/5 |
| 5,054,048 | * 10/1991 | Wang | 378/146 |
| 5,400,379 | 3/1995 | Pfoh et al. . | |
| 5,430,783 | 7/1995 | Hu et al. . | |
| 5,454,023 | * 9/1995 | Asikainen | 378/156 |
| 5,644,614 | 7/1997 | Toth et al. . | |
| 5,828,719 | * 10/1998 | He | 378/4 |

* cited by examiner

*Primary Examiner*—Teresa M. Arroyo
*Assistant Examiner*—Gioacchino Inzirillo
(74) *Attorney, Agent, or Firm*—Armstrong Teasdale LLP; Christian G. Cabou

(57) ABSTRACT

The present invention, in one form, is an imaging system which, in one embodiment, utilizes a filter assembly including a plurality of filter portions for altering the intensity and quality of an x-ray beam. Specifically, in one embodiment, by positioning the filter assembly so that the x-ray beam is filtered by the first portion of the filter assembly, the x-ray beam is altered to perform a body portion scan. By positioning the filter assembly to the second portion, the x-ray beam is altered to perform a head portion scan.

35 Claims, 4 Drawing Sheets

POSITION DEPENDENT BEAM QUALITY X-RAY FILTRATION

BACKGROUND OF THE INVENTION

This invention relates generally to computed tomography (CT) imaging and more particularly, to filtration of an x-ray beam in an imaging system.

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts that attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed.

The x-ray source is typically comprised of an evacuated glass x-ray tube containing an anode and a cathode. X-rays are produced when electrons from the cathode are accelerated against a focal spot on the anode by means of a high voltage across the anode and cathode.

The spectrum of the x-rays produced encompasses a band of radiation of differential frequencies having different energies. The short wavelength radiation of higher energy is referred to as "hard" x-ray radiation and the longer wavelength radiation of lower radiation is referred to as "soft" x-ray radiation. The very lowest energy x-rays are almost entirely absorbed by the body and therefore provide little contribution to the x-ray image. Nevertheless, these soft x-rays contribute to the total exposure of the patient to harmful ionizing radiation.

In at least one known CT system, a filter is used to remove or reduce the amount of "soft" x-rays. Filters are typically of a "fixed" type or a "shaped" type. The fixed filters are used to improve beam quality by removing soft x-rays which contribute to patient dose but do not contribute to image data measurement. Shaped filters are used to modify the x-ray intensity as a function of fan angle to obtain a more uniform x-ray intensity when a patient is present. The shaped filters are used to reduce x-ray intensity toward a patient extremity where less x-ray beam penetration is required. However, as a result of the different types and areas of the body to be scanned, selection of the ideal filter is difficult, if not impossible. As a result, the selected filter typically compromises either patient dose or beam quality.

Accordingly, it would be desirable to provide a filter which allows selection of filtration characteristics depending upon the scan to be completed. More specifically, the filter may be selectably configured to provide proper filtration for suitable x-ray beam quality and intensity for various types of scans.

BRIEF SUMMARY OF THE INVENTION

These and other objects may be attained in an imaging system which, in one embodiment, utilizes a filter assembly for altering the x-ray beam. Specifically, in one embodiment, the filter assembly includes a movable filter having a plurality of filter portions for altering the quality and intensity of the x-ray beam. Particularly, the filter material and physical shape of each filter portion is configured so that a different quality and intensity x-ray beam is generated from the filtered x-ray beam radiated from an x-ray source.

In operation, by positioning the movable filter so that the x-ray beam is filtered by the first portion of the filter assembly, the amount of soft x-rays and the intensity of the x-ray beam is altered to perform a selected type of scan, i.e., a body portion scan. By positioning the filter assembly to the second portion, the shape of the x-ray beam is altered to perform a different type of scan, i.e., a head scan.

By using the above described imaging system the x-ray beam quality and shape is alterable depending upon the scan to be completed. More specifically, the filtration characteristics of the imaging system may be selected to provide proper filtration for suitable x-ray beam quality and intensity for various types of scans.

DETAILED DESCRIPTION OF THE INVENTION

Figure 1:
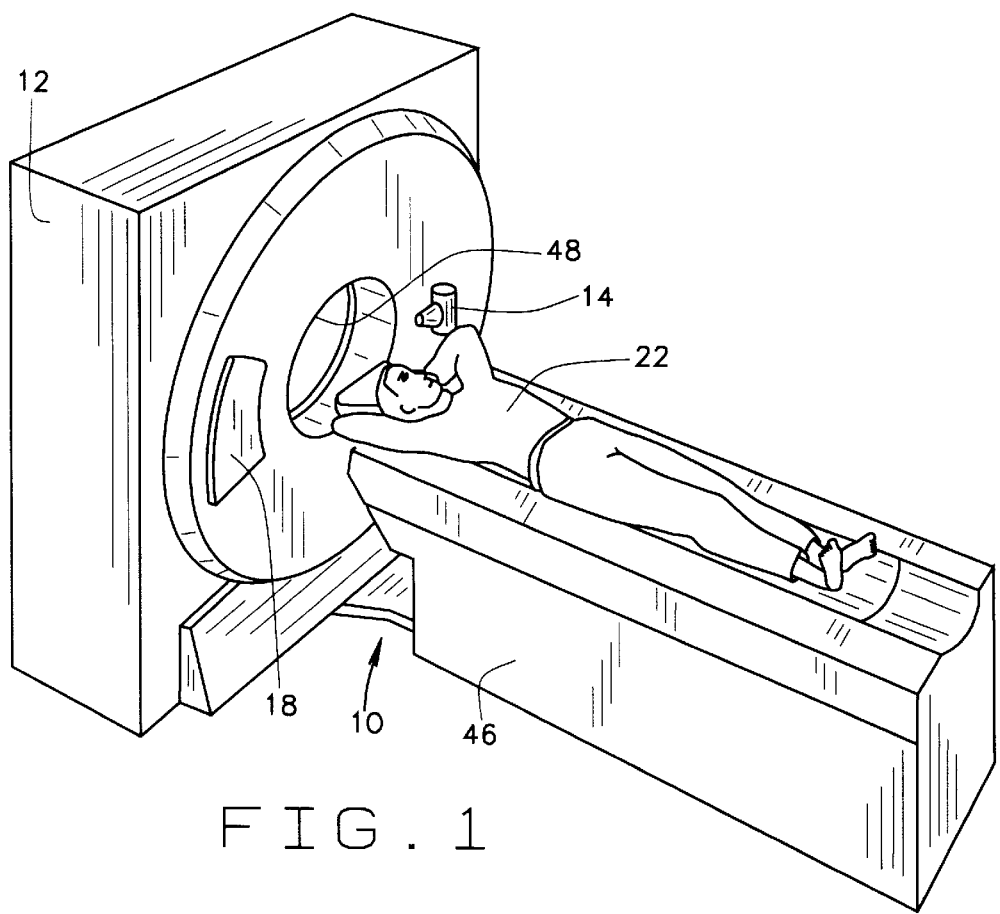
FIG. 1 is a pictorial view of a CT imaging system.
Figure 2:
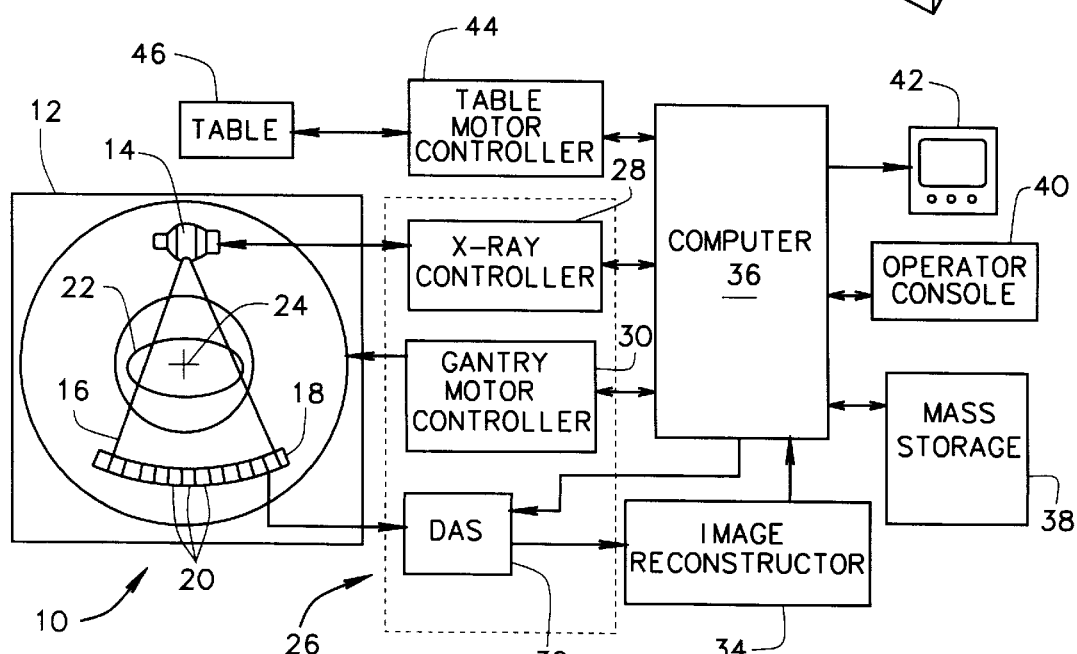
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives and supplies signals via a user interface, or graphical user interface (GUI). Specifically, computer receives commands and scanning parameters from an operator via console 40 that has a keyboard and a mouse (not shown). An associated cathode ray tube display 42 allows the operator to observe the reconstructed image and other data from computer 36. The operator supplied commands and parameters are used by computer 36 to provide control signals and information to x-ray controller 28, gantry motor controller 30, DAS 32, and table motor controller 44.

Figures 3, 4:
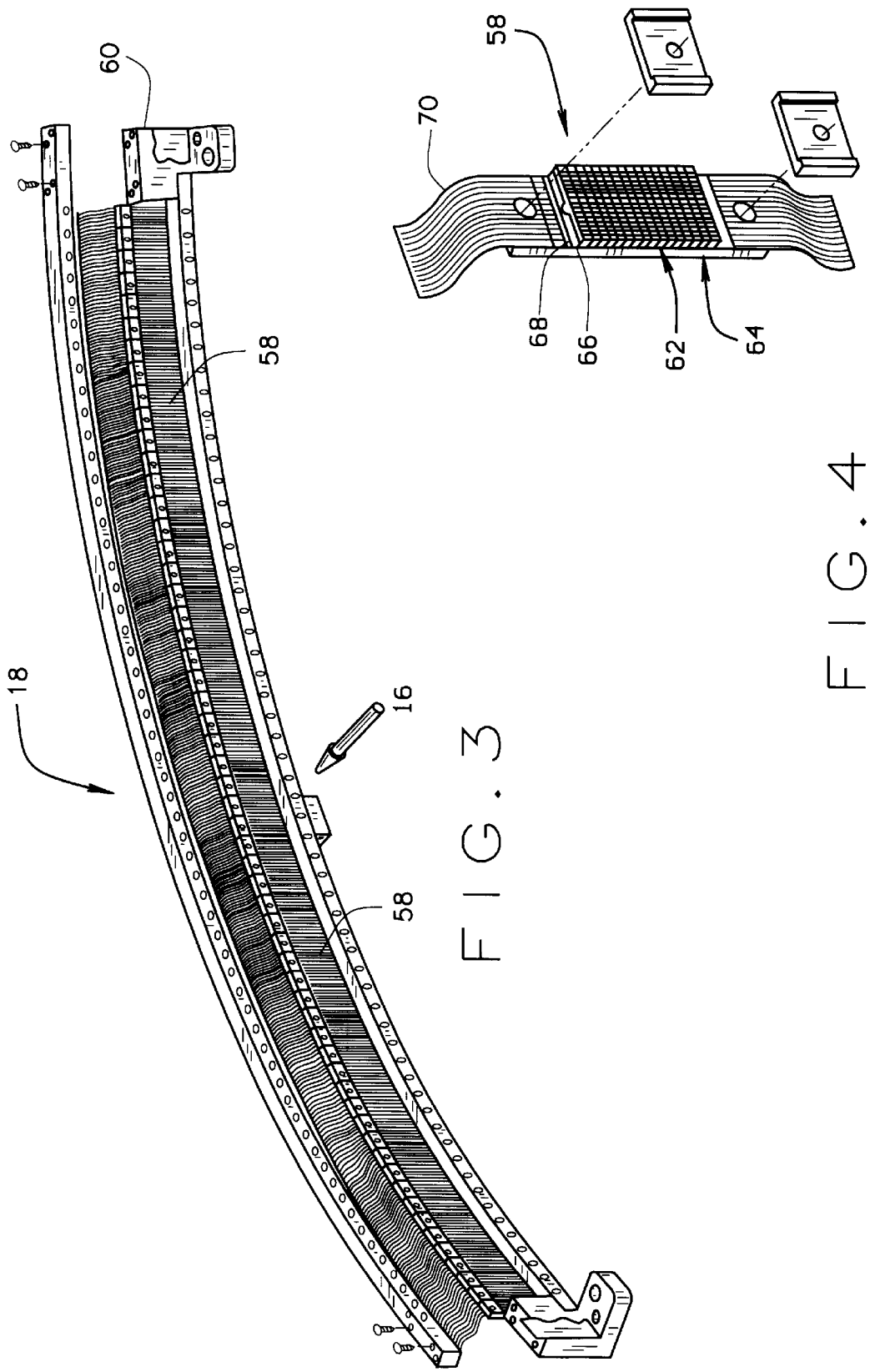
FIG. 3 is a perspective view of a CT system detector array.
FIG. 4 is a perspective view of a detector module.

As shown in FIGS. 3 and 4, detector array 18 includes a plurality of detector modules 58. Each detector module 58 is secured to a detector housing 60. Each module 58 includes a multidimensional scintillator array 62 and a high density semiconductor array (not visible). A post patient collimator (not shown) is positioned over and adjacent scintillator array 62 to collimate x-ray beams before such beams impinge upon scintillator array 62. Scintillator array 62 includes a plurality of scintillation elements arranged in an array, and the semiconductor array includes a plurality of photodiodes (not visible) arranged in an identical array. The photodiodes are deposited, or formed on a substrate 64, and scintillator array 62 is positioned over and secured to substrate 64.

Detector module 58 also includes a switch apparatus 66 electrically coupled to a decoder 68. Switch apparatus 66 is a multidimensional semiconductor switch array of similar size as the photodiode array. In one embodiment, switch apparatus 66 includes an array of field effect transistors (not shown) with each field effect transistor (FET) having an input, an output, and a control line (not shown). Switch apparatus 66 is coupled between the photodiode array and DAS 32. Particularly, each switch apparatus FET input is electrically connected to a photodiode array output and each switch apparatus FET output is electrically connected to DAS 32, for example, using flexible electrical cable 70.

Decoder 68 controls the operation of switch apparatus 66 to enable, disable, or combine the outputs of the photodiode array in accordance with a desired number of slices and slice resolutions for each slice. Decoder 68, in one embodiment, is a decoder chip or a FET controller as known in the art. Decoder 68 includes a plurality of output and control lines coupled to switch apparatus 66 and computer 36. Particularly, the decoder outputs are electrically connected to the switch apparatus control lines to enable switch apparatus 66 to transmit the proper data from the switch apparatus inputs to the switch apparatus outputs. The decoder control lines are electrically connected to the switch apparatus control lines and determine which of the decoder outputs will be enabled. Utilizing decoder 68, specific FETs within switch apparatus 66 are enabled, disable, or combined so that specific outputs of the photodiode array are electrically connected to CT system DAS 32. In one embodiment defined as a 16 slice mode, decoder 68 enables switch apparatus 66 so that all rows of the photodiode array are electrically connected to DAS 32, resulting in 16 separate, simultaneous slices of data being sent to DAS 32. Of course, many other slice combinations are possible.

In one specific embodiment, detector 18 includes fifty-seven detector modules 58. The semiconductor array and scintillator array 62 each have an array size of 16×16. As a result, detector 18 has 16 rows and 912 columns (16×57 modules), which enables 16 simultaneous slices of data to be collected with each rotation of gantry 12. Of course, the present invention is not limited to any specific array size, and it is contemplated that the array can be larger or smaller depending upon the specific operator needs. Also, detector 18 may be operated in many different slice thickness and number modes, e.g., one, two, and four slice modes. For example, the FETs can be configured in the four slice mode, so that data is collected for four slices from one or more rows of the photodiode array. Depending upon the specific configuration of the FETs as defined by decoder control lines, various combinations of outputs of the photodiode array can be enabled, disabled, or combined so that the slice thickness may, for example, be 1.25 mm, 2.5 mm, 3.75 mm, or 5 mm. Additional examples include a single slice mode including one slice with slices ranging from 1.25 mm thick to 20 mm thick, and a two slice mode including two slices with slices ranging from 1.25 mm thick to 10 mm thick. Additional modes beyond those described are possible.

Figure 5:
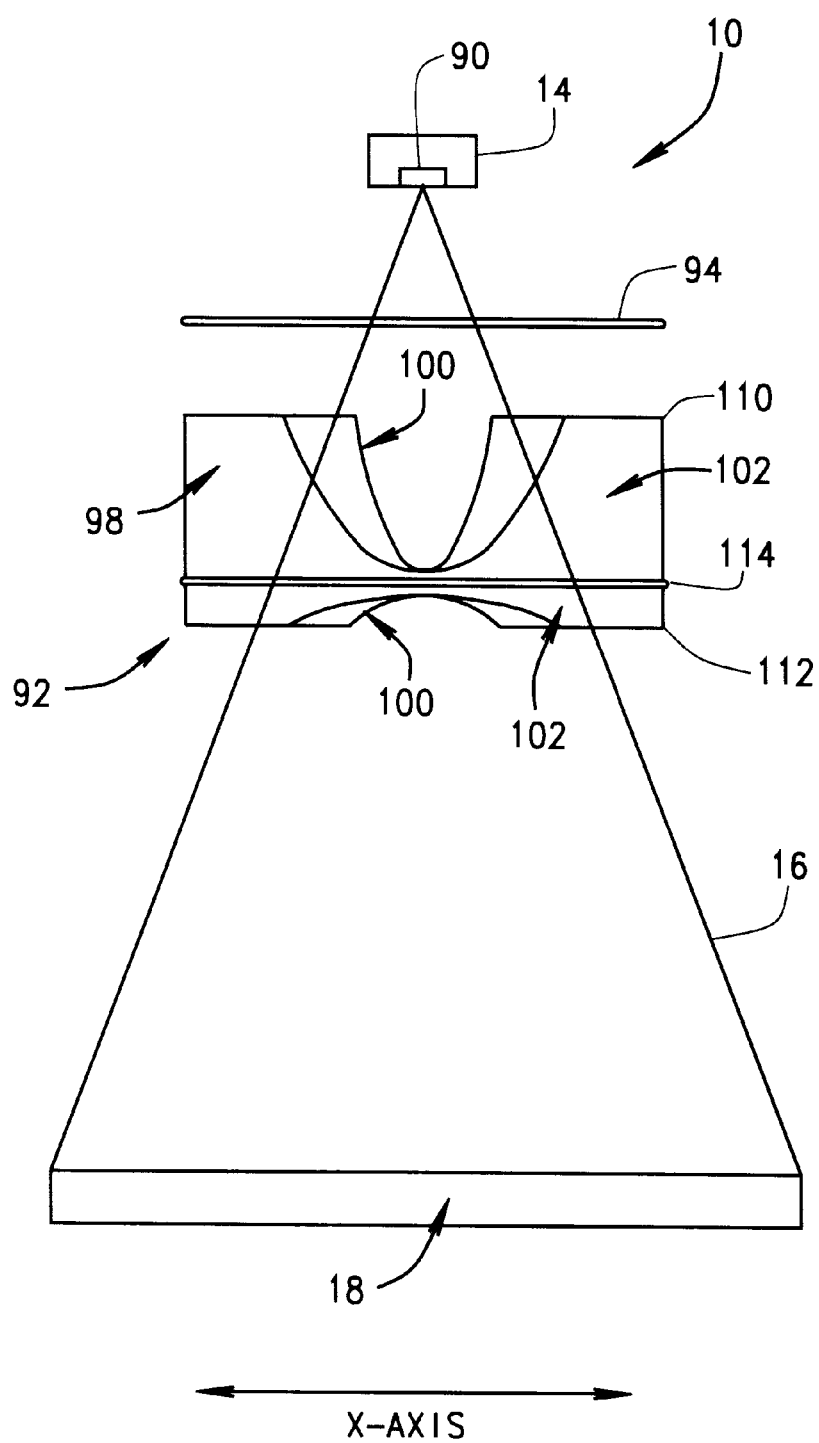
FIG. 5 is an x-axis schematic view of the CT imaging system shown in FIG. 1.
Figure 6:
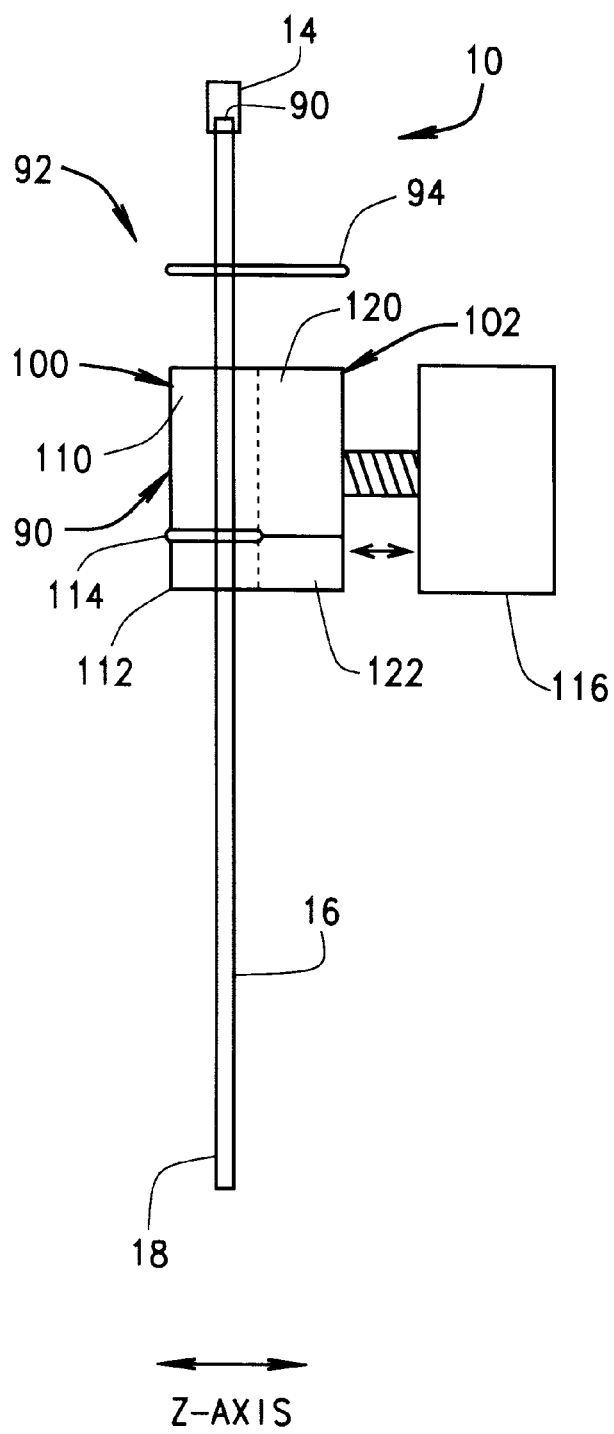
FIG. 6 is a z-axis schematic view of the CT imaging system shown in FIG. 5.

FIGS. 5 and 6 are schematic views of one embodiment of system 10 in accordance with the present invention. X-ray beam 16 emanates from a focal spot 90 of x-ray source 14. The intensity and quality of x-ray beam 16 is altered by filter assembly 92, and filtered beam 16 is projected toward detector array 18. More specifically and in one embodiment, filter assembly 92 includes a fixed filter portion 94, a z-axis movable filter 98 having a first portion 100 and a second portion 102. Respective portions 100 and 102 are configured to alter the intensity and quality of x-ray beam 16. More specifically, the shape and material composition of respective portions 100 and 102 are configured so that unique, or different, quality and intensity beams are created by filter assembly 92 based upon the position the movable filter 98.

Particularly, first portion 100 includes a first filter material 110, a second filter material 112 and a third filter material 114 positioned between, or interposed, materials 110 and 112. In one embodiment, first portion 100 is configured as a bowtie filter and respective materials 110, 112, and 114 are graphite, aluminum, and copper. For example, material 110 may be 54.0 mm thick, material 112 may be 6.0mm thick, and material 114 is about 75 micrometers thick so that first portion 100 is configured to generate a harder x-ray beam quality, for example to perform a body scan. In one embodiment, third layer 114 is positioned between layers 110 and 112 so that third layer 114 is protected from damaged during operation and handling. In alternative embodiments, materials 110, 112, and 114 may selected from other attenuating materials of various thicknesses. Further, one skilled in the art could select materials 110, 112, 114 from elements, compounds, or epoxy mixtures with approximately similar mass attenuation coefficients and adjust the thickness to compensate for material density differences. For example, material 110 (54 mm of graphite) could be substituted with 95 mm of polyethylene or material 114 (75 micrometers of copper) could be substituted with 325 micrometers of titanium.

Second portion 102, in one embodiment, includes a first filter material 120 and a second filter material 122. The physical configuration and selection for respective materials 120 and 122 are selected so that an x-ray beam radiating from second portion 102 has an intensity and quality unique from an x-ray beam radiating from first portion 100. In one embodiment, second portion 102 is configured to generate a softer x-ray beam quality and materials 120 and 122 are selected from the same materials as respective materials 110 and 112, however the physical shape of material 120 and 122 are altered. For example, second portion 102 is fabricated as a bowtie filter for generating a narrower x-ray beam and second portion filter material 120 is graphite and second filter material 122 is aluminum. Utilizing the described second portion 102, a head scan can be performed. In alternative embodiments, respective shape and filter materials 120 and 122 may be selected from other shapes and materials other than materials 110 and 112. In addition, similar to portion 100, second portion 102 may include any number of materials.

In one embodiment, filter assembly 92 further includes a drive assembly 116 coupled to movable filter 92. Drive assembly 116 is configured to alter the z-axis position of movable filter 92 so that the intensity and quality of x-ray beam 16 can be altered. Drive assembly, in one embodiment, is coupled to computer 36. In alternative embodiments drive assembly may also be coupled to a filter drive controller (not shown).

In operation, after selecting a scan type, movable filter 92 is positioned so that the proper x-ray beam is radiated toward patient 22, or an object. After collecting image data of the object or patient 22 using detector array 18, a reconstructed image is generated. More specifically, the scan type is initially determined using known selection criteria, or is prescribed by the operator, for example, a body scan. Utilizing the scan type information, movable filter 92 is positioned so that x-ray beam 16 is filtered using the appropriate portion of movable filter 92. More particularly and in one embodiment, an appropriate quality and intensity x-ray beam is generated by positioning movable filter 92 so that x-ray beam 16 is radiated into first portion 100, for example for a body scan. The z-axis position of movable filter 92 is adjusted by drive assembly 116.

If another type of scan is selected, for example, a head scan, the position of movable filter 92 is adjusted, or repositioned. More specifically, using drive assembly 116, the z-axis position of movable filter 92 is adjusted so that x-ray beam 16 is filtered by second portion 102. The filtering by second portion 102 alters the x-ray beam so that, for example for the head scan, x-ray beam 16 radiated toward detector array 18 is narrower and the beam quality is softer.

Utilizing portions 100 and 102, x-ray beam 16 is filtered so that the proper x-ray beam intensity and quality is directed toward detector array 18. In alternative embodiments, movable filter 92 may include any number of portions so that any number of unique quality and intensity beams may be radiated toward patient 22 and detector array 18. The above described filter assembly allows selection of filtration characteristics depending upon the scan to be completed. More specifically, the filter assembly includes a plurality of filters so that the proper filtration is provided for various specific types of scans, i.e., head portion scans or body portion scans.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used. Similarly, while the systems described herein have been two-slice and four-slice, any multi-slice system may be used. Accordingly, the spirit and scope of the invention are to be limited only by the terms of the appended claims.

What is claimed is:

1. An x-ray beam filter assembly for an imaging system, the imaging system including a detector array and an x-ray source for radiating an x-ray beam toward the detector array, said filter assembly comprising:
a fixed filter portion; and
a z-axis movable filter comprising a plurality of portions, wherein each portion configured to alter the x-ray beam intensity and quality.

2. A filter assembly in accordance with claim 1 wherein said movable filter comprises a first portion configured to alter the x-ray beam into a first beam and a second portion configured to alter the x-ray beam into a second beam.

3. A filter assembly in accordance with claim 1 further comprising a drive assembly coupled to said movable filter and configured to alter the z-axis position of said movable filter.

4. A filter assembly in accordance with claim 2 wherein said first portion comprises at least one filter material and said second portion comprises at least a first filter material.

5. A filter assembly in accordance with claim 2 wherein said first portion configured to generate a harder x-ray beam quality.

6. A filter assembly in accordance with claim 2 wherein said second portion configured to generate a softer x-ray beam quality.

7. A filter assembly in accordance with claim 4 wherein said first portion comprises a first filter material, a second filter material and a third filter material.

8. A filter assembly in accordance with claim 4 wherein said second portion comprises a first filter material and a second filter material.

9. A filter assembly in accordance with claim 5 wherein said first portion configured to perform a body scan.

10. A filter assembly in accordance with claim 6 wherein said second portion configured to perform a head scan.

11. A filter assembly in accordance with claim 7 wherein said third material is positioned between said first portion first filter material and said first portion second filter material.

12. A filter assembly in accordance with claim 8 wherein said second portion first filter material comprises graphite and said second portion second filter material comprises aluminum.

13. A filter assembly in accordance with claim 11 wherein said first portion first filter material comprises graphite, said first portion second filter material comprises aluminum, and said first portion third material comprises copper.

14. A filter assembly in accordance with claim 13 wherein said first portion third filter material has a thickness of about 75 micrometers.

15. A method for altering an x-ray beam in an imaging system, the imaging system including a detector array; an x-ray source for radiating an x-ray beam toward the detector array; and a filter assembly including a movable filter having a plurality of portions each configured to alter the x-ray beam intensity and quality, and a fixed filter portion; said method comprising the steps of:

selecting a scan type;

positioning the movable filter;

filtering the x-ray beam through the fixed filter portion and the positioned movable filter; and performing an object scan.

16. A method in accordance with claim 15 wherein the movable filter comprises a first portion configured to alter the x-ray beam into a first beam and a second portion configured to alter the x-ray beam into a second beam, and wherein positioning the movable filter comprising the step of positioning the movable filter so that the x-ray beam is filtered by the movable filter first portion.

17. A method in accordance with claim 15 wherein selecting a scan type comprises the step of selecting a body scan.

18. A method in accordance with claim 15 wherein selecting a scan type comprises the step of selecting a head scan.

19. A method in accordance with claim 16 wherein positioning the movable filter further comprises the step of positioning the movable filter so that the x-ray beam is filtered by the movable filter second portion.

20. A method in accordance with claim 16 wherein the filter assembly further includes a drive assembly coupled to the movable filter, and wherein positioning the movable filter so that the x-ray beam is filtered by the movable filter first portion comprises the step of altering the position of the movable filter with the drive assembly.

21. A method in accordance with claim 20 wherein positioning the movable filter so that the x-ray beam is filtered by the movable filter second portion comprises the step of altering the position of the movable filter with the drive assembly.

22. A method for altering an x-ray beam in an imaging system, the imaging system including a detector array, an x-ray source for radiating an x-ray beam toward the detector array and a filter assembly including a movable filter having a plurality of portions, wherein the first portion comprises a first filter material, a second filter material and a third filter material positioned between the first filter material and the second filter material, and the movable filter first portion configured to alter the x-ray beam into a first beam and the second portion configured to alter the x-ray beam into a second beam, said method comprising the steps of:

selecting a scan type;

positioning the movable filter so the x-ray beam is filtered by the movable filter first portion; and performing an object scan.

23. An imaging system including a detector array; an x-ray source for radiating an x-ray beam toward the detector array; and a filter assembly including a movable filter having a plurality of portions each configured to alter the x-ray beam intensity and quality, and a fixed filter portion; said imaging system configured to:

determine a scan type;

position the movable filter;

filter the x-ray beam through the fixed filter portion and the positioned movable filter; and perform an object scan.

24. A system in accordance with claim 23 wherein said movable filter includes a first portion configured to alter the x-ray beam into a first beam and a second portion configured to alter the x-ray beam into a second beam, and wherein to position said movable filter, said system configured to position the movable filter so that the x-ray beam is filtered by said first portion.

25. A system in accordance with claim 23 wherein to select a scan type, said system is configured to obtain scan type from an operator.

26. A system in accordance with claim 23 wherein said detector array is a multislice detector array.

27. A system in accordance with claim 23 wherein said scan is helical scan.

28. A system in accordance with claim 24 wherein said imaging system further includes a drive assembly coupled to said movable filter and wherein to position the movable filter so that the x-ray beam is filtered by said first portion, said system configured to alter position of said movable filter with said drive assembly.

29. A system in accordance with claim 25 wherein obtained scan type is a body scan.

30. A system in accordance with claim 25 wherein obtained scan type is a head scan.

31. A system in accordance with claim 28 wherein to position said movable filter so that the x-ray beam is filtered by said the second portion, said system configured to alter the position of the movable filter with the drive assembly.

32. An imaging system including a detector array, an x-ray source for radiating an x-ray beam toward the detector array and a filter assembly including a movable filter having a plurality of portions, wherein said first portion comprises a filter first material, a second filter material and a third filter material positioned between said first filter material and said second filter material, and said movable filter first portion configured to alter the x-ray beam into a first beam and said second portion configured to alter the x-ray beam into a second beam, said imaging system configured to:

determine a scan type;

position the movable filter so that the x-ray beam is filtered by said first portion; and perform an object scan.

33. A system in accordance with claim 32 wherein to position said movable filter, said system further configured to position said movable filter so that the x-ray beam is filtered by said second portion.

34. An imaging system in accordance with claim 32 wherein said detector array is a multislice detector array.

35. An imaging system in accordance with claim 32 wherein said scan is a helical scan.

* * * * *

UNITED STATES PATENT AND TRADEMARK OFFICE
CERTIFICATE OF CORRECTION

PATENT NO.    : 6,307,918 B1  Page 1 of 1
DATED         : October 23, 2001
INVENTOR(S)   : Thomas L. Toth et al.

It is certified that error appears in the above-identified patent and that said Letters Patent is hereby corrected as shown below:

<u>Title page,</u>
Item [75], Inventors, change the name of "Carmine F. Vara" to
-- Carmine F. Vara Jr. --.

<u>Column 3,</u>
Line 37, delete "that".
Line 67, delete "disable" and insert therefor -- disabled --.

<u>Column 4,</u>
Line 57, delete "damaged" and insert therefor -- damage --.
Line 58, after "may" insert -- be --.

Signed and Sealed this

Twenty-fourth Day of June, 2003

JAMES E. ROGAN
*Director of the United States Patent and Trademark Office*